April 20, 1937. H. F. GREIDER Plant Pat. 247

BERRY

Filed Feb. 11, 1935

HALLACK F. GREIDER INVENTOR

BY Cook & Robinson

ATTORNEY

Patented Apr. 20, 1937

UNITED STATES PATENT OFFICE

247

BERRY

Hallack F. Greider, Vashon, Wash.

Application February 11, 1935, Serial No. 5,985

1 Claim. (Cl. 47—62)

This invention relates to a new and distinct variety of berry of the character of the loganberry or blackberry, and produced by artificial pollination of a Burbank "Phenomenal" berry with the pollen of the Plum Farmer black cap or black raspberry; the object of the invention being to produce a berry plant that is sturdy and long lived and produces a fruit having all of the desirable characteristics of the fruit of the parent plants with respect to taste and edibility; that will keep better and longer especially in storage; which plant is sturdy and long lived and practically everbearing.

Figure 1:
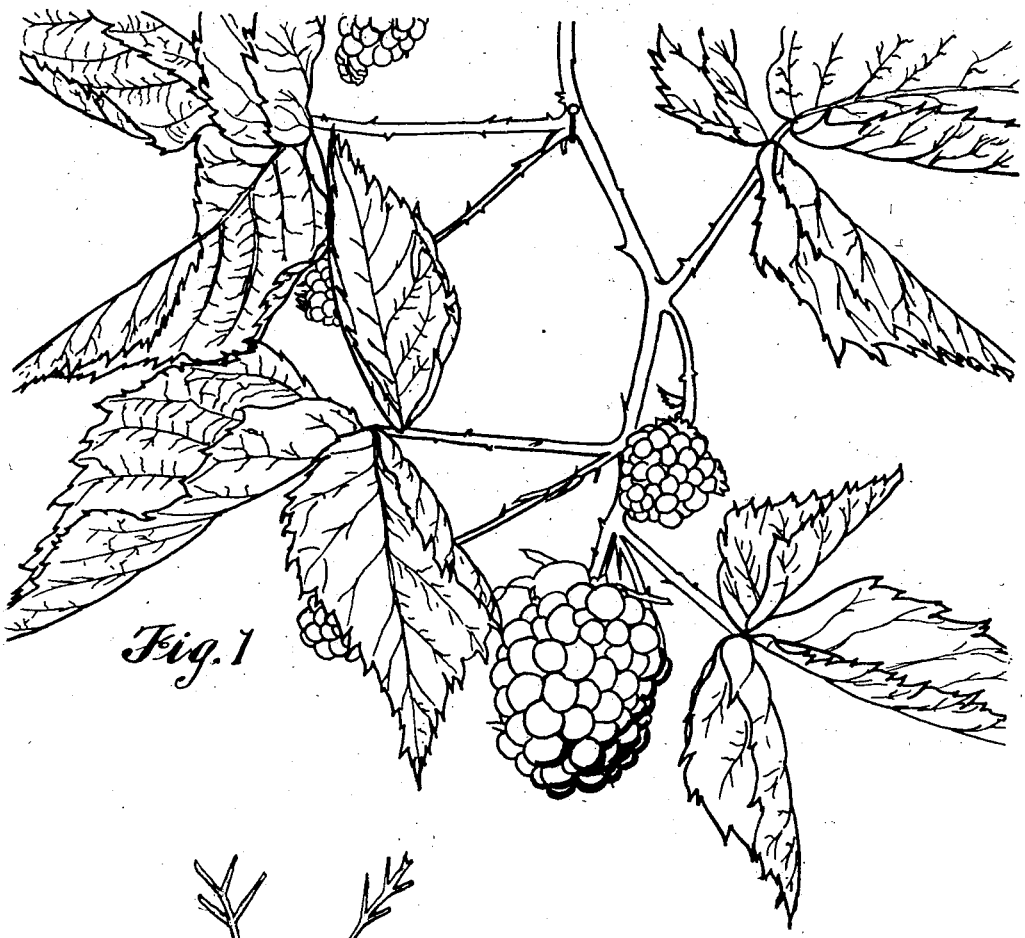
Figure 2:
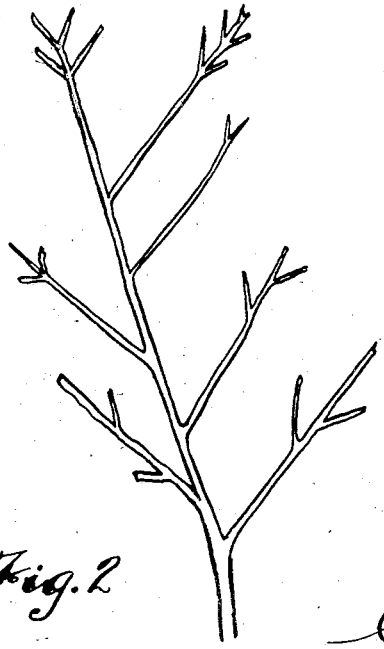

In the accompanying drawing, Fig. 1 is a full size view of leaves and berry. Fig. 2 is an illustration of a plant stalk.

To obtain these results, the pollen of the black raspberry was put in the blossom of the "Phenomenal" berry, then the pollinated blossoms were protected so that they could receive no pollen of any other plant. These flowers were allowed to develop into fruit, and the seeds from this fruit were planted and allowed to sprout. When the plants had grown to sufficient size they were transplanted and allowed to grow for three years, at the end of which time, the fruit of each plant was individually tested and that particular vine which produced the most satisfying fruit was saved and all others destroyed. One vine from the plant that was saved was tipped; that is, the tip end was buried in the ground and this took root and produced a new plant. All the plants that are now growing have come from this original plant.

The characteristics of the plant are as follows: From six to fifteen very thorny canes of reddish brown color grow up from each plant. These canes grow almost straight up for three or four feet and then arch over to the ground. These main canes or stalks have many laterals and the laterals quite often have branches. There is no regularity with respect to the side or lateral branches, and if they do not appear near the butt end of the main stalk they appear at its outer end and grow to a length equal to the main stalk. These canes are quite stiff and if allowed to remain uncovered during winter months they become tough but not brittle.

The leaves appearing on the vines are quite large, and of dark green color and have the characteristic of remaining green all winter. They do not dry up or turn brown, and if anything, are brighter at the end of the season than at the beginning.

The fruit spurs, or shoots, on which the fruit grows appear approximately every two to three inches and are of various lengths and grow close to the ground, thereby giving the plant a bush like appearance. These fruiting shoots are thick and heavy and stiff, no matter at which angle they grow and they do not normally overlap. After the berry season is over, more long shoots will grow out at any place along the vine and these shoots will produce fruit. Shoots from six to eight feet long will have as many as twenty-five berries on them. Thus, at the same time the plant will have blossoms, green fruit and ripe fruit. The long fruit shoots, however, have a different appearance and texture than the ordinary shoot. They are reddish brown in color as distinguished from the green of the ordinary shoot.

The blossoms are large and from two to two and one-half inches in diameter.

The berries produced by this plant are similar in appearance to the blackberry but very large. Some get two inches long and over an inch in diameter; the average berry being from one and one-quarter inch to one and one-half inch in length and three-fourths to one inch in diameter and having symmetrically rounded or blunt ends and not pointed at one one, as is the blackberry or loganberry. Their color when ripe is wine black, but when dead ripe they are a shiny black. Berries are firm and do not get mushy or soft on the vine no matter how long they remain. In time the lobes which are large and irregular in setting, separate and shrivel up.

The core of the berry is large but disappears with cooking. The seeds are large but are not noticeable in eating; in fact, the core and seeds are not distasteful and are not apparent to one eating the berry. Cooking does not destroy the unity of the berry.

In the natural state, ripe berries are sweet enough for table use. The flavor is a sort of mixture of the wild blackberry and black cap. Sometimes, it resembles one or the other of these individually. The first berries ripen in July ordinarily, sometimes earlier and sometimes later depending on the weather. The plant, however, is almost ever-bearing as it produces fruit for several months and just the end of the vine producing fruit dies while the rest of the vine produces fruit the following year.

The plants are now being grown in the Puget Sound region of Washington and thrive in the climate of that location.

Further information:—

Plant:
*Size.*—Tall.
*Vigor.*—Vigourous.
*Habit.*—Spreading, trailing, dense.
*Propagation.*—By tips.
*Hardiness.*—Half hardy.
*Productiveness.*—Very productive.
*Susceptibility.*—To insects, none.
—To diseases, very slightly to anthracnose.
*Suckers.*—Medium.
*Canes.*—Biennial.
*Diameter.*—Stocky.
*Number.*—Numerous.
*Shape.*—Cylindrical.
*Color.*—Greenish, pubescent.
*Glaucousness.*—Thin, eglandular.
*Prickles.*—Medium length, slender, medium strength, straight, numerous; color—greenish white.
*Branches.*—Medium in number.
Leaves:
*Fall.*—Late.
Evergreen.
Deciduous.
Variable with season's moisture.
3-leaved, 5-leaved or 7-leaved.
Leaflets:
*Size.*—Large.
*Shape.*—Ovate.
*Width.*—Wide.
*Length.*—Long.
*Thickness.*—Medium.
Terminal leaflets:
Variable.
*Base.*—Cordate.
*Shape.*—Ovate.
*Apex.*—Taper-pointed.
Upper surface:
*Color.*—Dark green.
Pubescent.
Lower surface:
*Color.*—Whitish.
Tomentose.
Midrib:
Prickly.
Margin:
Serrate.
Lobed.
Double series.
Stalk of leaflet:
Tomentose.
Prickly.
Petiole:
*Length.*—Medium.
*Thickness.*—Slender.
Pubescent.
*Prickles.*—Many, slender, straight.
Flowers:
*Date of bloom.*—May 10 to July 22.
*Season of bloom.*—Medium to late, still blooming in fall.
*Size.*—Medium.
*Color.*—White.
*Number in cluster.*—Medium.
*Form of cluster.*—Long, open, leafy.
*Pedicels.*—Long, slender, pubescent, prickly; prickles straight.
*Petals.*—Length 15 mm., medium, oval.
*Calyx.*—Medium, flat, white, glabrous, eglandular; prickles straight.
Fruit:
*Season.*—Midseason.
*Date of ripening.*—July 8.
*Length of season.*—Two months.
*Number of pickings.*—Depends on weather; ten in year 1935.
*Keeping quality.*—Excellent.
*Shipping quality.*—Very good.
*Susceptibility.*—To insects, excellent resistance.
—To diseases, very slight.
—To drought, very good resistance.
—To sunscald, none.
*Adherence.*—Clings well.
*Picking quality.*—
*Size.*—Very large.
*Shape.*—Cylindrical.
*Drupelets.*—
*Size.*—Large.
*Shape.*—Pyriform.
*Number.*—Medium.
*Coherence.*—Strong.
*Color.*—Dark red to black.
*Juice.*—Juicy.
*Texture.*—Firm.
*Flavor.*—Mild, aromatic.
*Quality.*—Best.
*Core.*—Soft.
*Use.*—Dessert, market, canning.
Classification:
Dewberry (locally called a blackberry).

In comparison with the Young dewberry, the present berry is larger in average size, superior in appearance and much more uniform in size and shape, and the berries remain large in size throughout the entire fruiting season, whereas the Young berries late in the season are much smaller. The present berry plant is a much heavier bearer than the Young plant and is hardier and unaffected by severe winter conditions where the Young plant will be killed.

I claim:

The berry substantially as herein disclosed, characterized by its hardiness and prolific fruiting.

HALLACK F. GREIDER.